(12) United States Patent
Nukui

(10) Patent No.: US 7,336,759 B2
(45) Date of Patent: Feb. 26, 2008

(54) SCATTERING COMPENSATING METHOD AND SCATTERING MEASURING METHOD

(75) Inventor: Masatake Nukui, Tokyo (JP)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 0 days.

(21) Appl. No.: 11/365,249

(22) Filed: Mar. 1, 2006

(65) Prior Publication Data

US 2006/0198489 A1 Sep. 7, 2006

(30) Foreign Application Priority Data

Mar. 1, 2005 (JP) ............................. 2005-056083

(51) Int. Cl.
*H05G 1/60* (2006.01)
(52) U.S. Cl. ............................. 378/7; 378/86; 378/207; 378/901
(58) Field of Classification Search .................. 378/4, 378/7, 86, 207, 901
See application file for complete search history.

(56) References Cited

U.S. PATENT DOCUMENTS

| | | | | |
|---|---|---|---|---|
| 4,352,020 | A * | 9/1982 | Horiba et al. .................. | 378/18 |
| 4,881,251 | A * | 11/1989 | Nambu et al. .................. | 378/7 |
| 4,887,285 | A * | 12/1989 | Harding et al. ................ | 378/88 |
| 5,602,895 | A * | 2/1997 | Fivez et al. ................... | 378/98.4 |
| 6,173,033 | B1 * | 1/2001 | Klingenbeck-Regn et al. ... | 378/20 |
| 6,639,964 | B2 * | 10/2003 | Schneider et al. .............. | 378/7 |
| 6,789,943 | B2 * | 9/2004 | Zapalac ....................... | 378/207 |
| 6,845,147 | B2 * | 1/2005 | Elam et al. ................... | 378/86 |
| 7,136,450 | B2 * | 11/2006 | Ying et al. ..................... | 378/7 |
| 7,190,758 | B2 * | 3/2007 | Hagiwara ..................... | 378/7 |
| 2003/0198314 | A1 * | 10/2003 | Saito ............................ | 378/4 |
| 2005/0063518 | A1 | 3/2005 | Nukui ......................... | 378/207 |
| 2005/0074087 | A1 | 4/2005 | Nukui ............................ | 378/7 |
| 2005/0147200 | A1 | 7/2005 | Nukui ........................... | 378/7 |

FOREIGN PATENT DOCUMENTS

| | | |
|---|---|---|
| JP | 07-213517 | 8/1995 |
| JP | 08-131431 | 5/1996 |
| JP | 11-299768 | 11/1999 |

* cited by examiner

*Primary Examiner*—Courtney Thomas
*Assistant Examiner*—Alexander Taningco
(74) *Attorney, Agent, or Firm*—Armstrong Teasdale LLP

(57) ABSTRACT

A method for compensating scattering includes acquiring the projective length of non-subject entities and acquiring the projective length of an object of radiography wherein the object of radiography is radiographed with a beam thickness set to the same value as a detector thickness and the object of radiography is radiographed with the beam thickness set to a value larger than the detector thickness. An amount of scattering is calculated based on the difference between the object data from the first scan and the object data from the second scan and stored in association with the sum of projective lengths. A subject is radiographed to produce data and the projective length of the subject is calculated along with the projective length of the non-subject entities having affected the data. The amount of scattering associated with the sum of the projective length and the projective length is then determined.

20 Claims, 6 Drawing Sheets

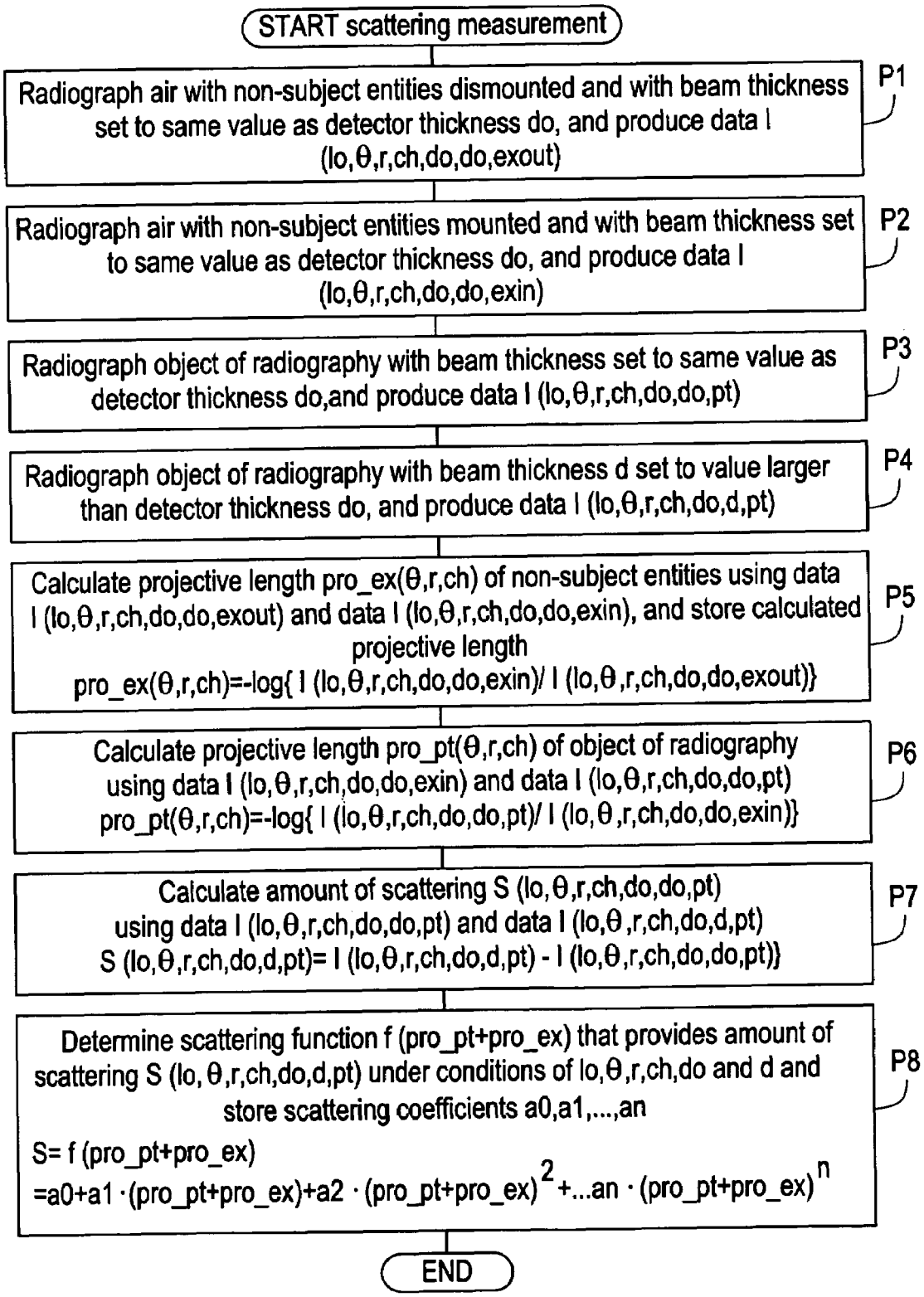

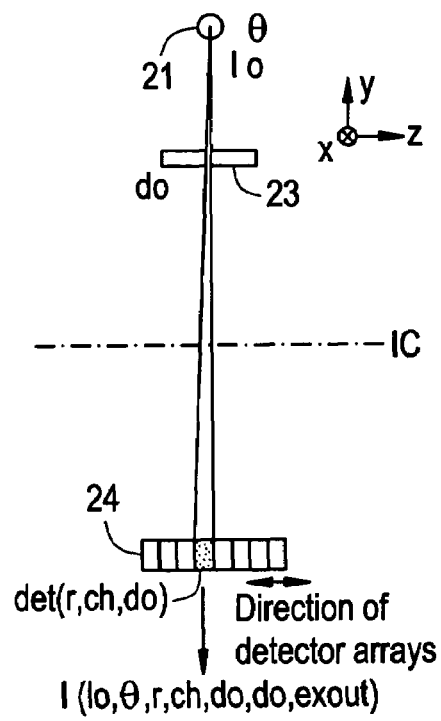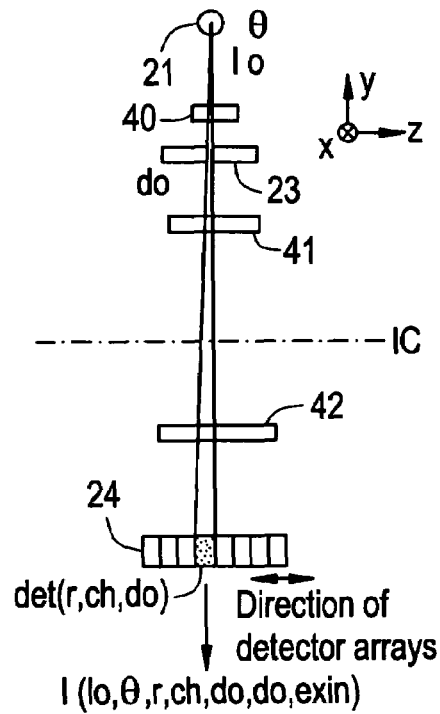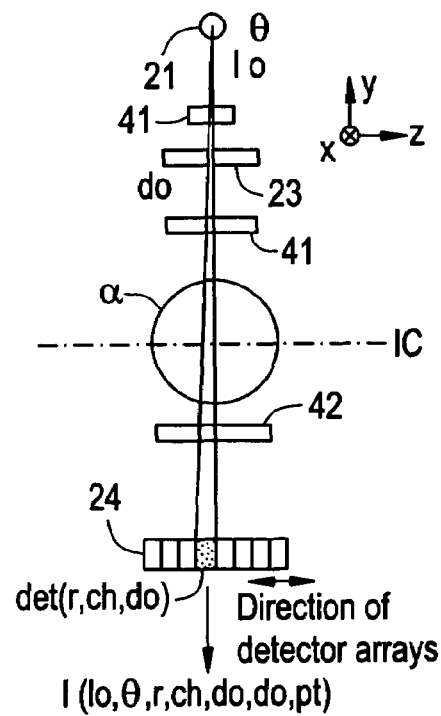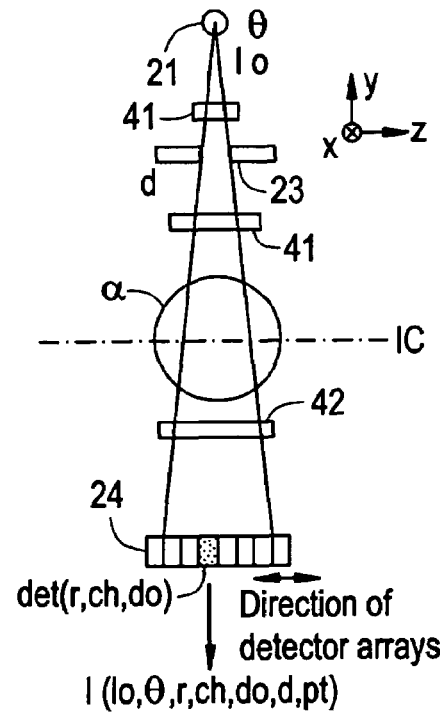

FIG. 4
| θ,r | |
|---|---|
| ch | pro_ex |
| | |
| | |
| | |
| | |
| | |
| | |
| | |
| | |
FIG. 5
| kV(Io),θ,r,ch,do,d | | | | | | |
|---|---|---|---|---|---|---|
| W = pro_pt+pro_ex | a0 | a1 | a2 | a3 | ... | an |
| | | | | | | |
| | | | | | | |
| | | | | | | |
| | | | | | | |
| | | | | | | |
| | | | | | | |
| | | | | | | |
| | | | | | | |
FIG. 6A
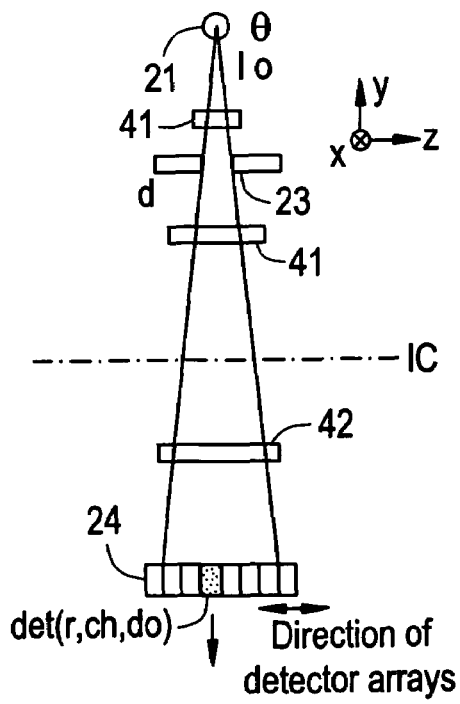
FIG. 6B
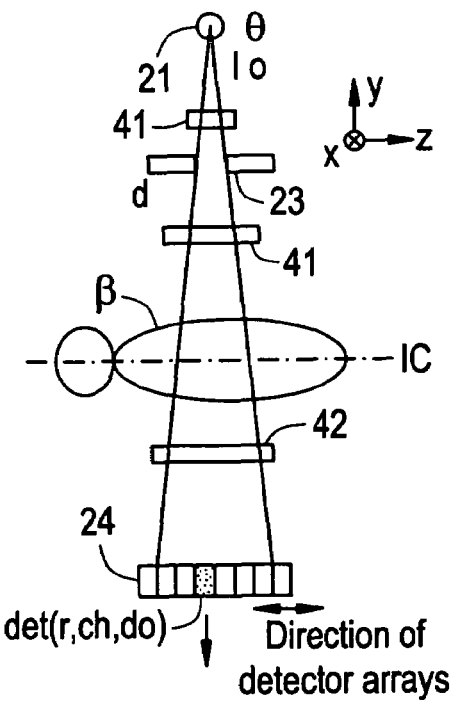

SCATTERING COMPENSATING METHOD AND SCATTERING MEASURING METHOD

CROSS REFERENCE TO RELATED APPLICATIONS

This application claims the benefit of Japanese Application No. 2005-056083 filed Mar. 1, 2005.

BACKGROUND OF THE INVENTION

The present invention relates to a scattering compensating method, a scattering measuring method, and an X-ray computed tomography (CT) system. More particularly, the present invention is concerned with a scattering compensating method, a scattering measuring method, and an X-ray CT system for compensating the adverse effect of scattering occurring during multi-slice radiography.

In the past, various scattering compensating methods adaptable to X-ray CT systems employing a single-channel X-ray detector have been known (refer to, for example, Patent Document 1 and Patent Document 2).

Moreover, a scattering compensating method adaptable to X-ray CT systems employing a multi-channel X-ray detector has been proposed (refer to, for example, Patent Document 3).

[Patent Document 1] Japanese Unexamined Patent Publication No. 7-213517

[Patent Document 2] Japanese Unexamined Patent Publication No. 8-131431

[Patent Document 3] Japanese Unexamined Patent Publication No. 11-299768

When a multi-channel X-ray detector having a plurality of detector arrays is used to perform multi-slice radiography, the thickness of a beam is larger than the thickness of each detector (or each detector array). Accordingly, the adverse effect of scattering is intensified.

However, a conventional scattering compensating method for X-ray CT systems employing a single-channel X-ray detector does not take account of the foregoing case and cannot be applied to the case.

Moreover, a conventional scattering compensating method for X-ray CT systems employing a multi-channel X-ray detector can be applied to the foregoing case but requires two image reconstructions. Thus, this method imposes a large load of processing.

SUMMARY OF THE INVENTION

An object of the present invention is to provide a scattering compensating method for compensating the adverse effect of scattering occurring during multi-slice radiography, a scattering measuring method for measuring an amount of scattering, and an X-ray CT system.

According to the first aspect of the present invention, there is provided a scattering compensating method comprising the steps of: acquiring a projective length pro_ex of non-subject entities that are entities other than a subject, the entities causing scattering of X-rays which cannot be ignored while existing in a passage of X-rays during radiography of a subject; acquiring a projective length pro_pt of an object of radiography; measuring data I(do,do) by performing radiography with the non-subject entities and the object of radiography inserted the passage of X-rays and with a beam thickness set to the same value as a detector thickness do; measuring data I(do,d) by radiographing the object of radiography with the beam thickness set to a value d larger than the detector thickness do; calculating an amount of scattering S(do,d) on the basis of a difference between the data I(do,do) and the data I(do,d); storing information needed to calculate the amount of scattering S(do,d) using the projective length pro_ex of the non-subject entities and the projective length pro_pt of the object of radiography; radiographing the subject so as to produce data, and using the data to calculate the projective length pro_pt of the subject and the projective length pro_ex of the non-subject entities having affected the data; and reading the information associated with the projective length pro_pt of the subject and the projective length pro_ex of the non-subject entities, and using the information to correct the data so as to compensate scattering.

In the foregoing method, the object of radiography is normally a phantom but may be a subject. Moreover, parameters written in parentheses in order to distinguish data I(do,do), data I(do,d), or the amount of scattering S(do,d) denote a detector thickness and a beam thickness respectively.

In the scattering compensating method in accordance with the first aspect, the detector thickness do is held unchanged but the beam thickness d alone is modified. Therefore, an increment from the data I(do,do) to the data I(do,d) is thought to attribute to scattering. Consequently, the amount of scattering S(do,d) can be calculated based on the difference between the data I(do,do) and the data I(do,d). Incidentally, scattering represented by the data I(do,do) is ignored. Otherwise, since the data I(do,do) is regarded as data produced by the single-channel X-ray detector, scattering represented by the data I(do,do) may be compensated according to the conventional scattering compensating method.

Scattering of X-rays occurring during radiography of a subject is caused by non-subject entities such as a filter and covers and the subject existing in the passage of X-rays. The projective length proj_ex of the non-subject entities (equal to a product of an X-ray absorption coefficient by an X-ray transmissive length) and the projective length pro_pt of the subject express the property of the non-subject entities and the property of the subject respectively, and are thought to correlate with an amount of scattering S(do,d). Therefore, the correlation among the projective length pro_ex of the non-subject entities, the projective length pro_pt of the object of radiography, and the amount of scattering S(do,d) is defined, and the information on the correlation is stored in association with the projective length pro_ex of the non-subject entities and the projective length pro_pt of the object of radiography.

As the information, the amount of scattering S(do,d) may be directly stored. Otherwise, so-called indirectly, a function formula for use in calculating the amount of scattering S(do,d) using the projective length pro_ex of the non-subject entities and the projective length pro_pt of the object of radiography or parameters (coefficients) that define the function formula may be stored. The ratio of the amount of scattering S(do,d) to data or a value calculated by subtracting the ratio from 1, that is, the ratio of a value calculated by subtracting the amount of scattering S(do,d) from the data may be stored.

Moreover, the information on the correlation may be stored in so-called indirect association with a parameter calculated based on the projective length pro_ex of the non-subject entities and the projective length pro_pt of the object of radiography instead of being stored in direct association with the projective length pro_ex of the non-subject entities and the projective length pro_pt of the object of radiography. The parameter may be, for example, a sum of projective lengths pro_pt+pro_ex, that is, the sum of the projective length pro_ex of the non-subject entities and the projective length,pro_pt of the object of radiography (information on each detector). Otherwise, the parameter may be a value calculated by adding up the sums of projective lengths pro_pt+pro_ex calculated relative to detectors belonging to all detector arrays and being included in the channel in which a detector concerned is included (information on each channel), a value calculated by adding up the sums of projective lengths pro_pt+pro_ex calculated relative to detectors that belong to a plurality of detector arrays including the detector array to which the detector concerned belongs and that are included in the channel in which the detector concerned is included (information on each detector), a value calculated by adding up the sums of projective lengths pro_pt+pro_ex calculated relative to detectors that are included in all channels and that belong to the detector array to which the detector concerned belongs (information relative to each detector array), a value calculated by adding up the sums of projective lengths pro_pt+pro_ex calculated relative to detectors that are included in a plurality of channels including the channel in which the detector concerned is included and that belong to the detector array to which the detector concerned belongs (information on each detector), a value calculated by adding up the sums of projective lengths pro_pt+pro_ex calculated relative to detectors that are included in a plurality of channels including the channel in which the detector concerned is included and that belong to a plurality of detector arrays including the detector array to which the detector concerned belongs (information on each detector), or a value calculated by adding up the sums of projective lengths pro_pt+pro_ex calculated relative to all detectors (information shared by all the detectors).

A subject is radiographed in order to produce data, and the projective length pro_pt of the subject is calculated using the data. Moreover, the projective length pro_ex of the non-subject entities having affected the data is calculated (the projective length pro_ex is determined with the geometric relationship between a detector having produced the data and the non-subject entities). Thereafter, information stored in association with the projective length pro_pt of the subject and the projective length pro_ex of the non-subject entities is read out. Consequently, an amount of scattering can be inferred from the information, and the produced data can be corrected in order to compensate scattering.

According to the second aspect of the present invention, there is provided a scattering compensating method according to which information needed to calculate an amount of scattering S(do,d) using the projective length pro_ex of non-subject entities that are entities other than a subject and the projective length pro_pt of an object of radiography is stored, the entities causing scattering of X-rays which cannot be ignored while existing in the passage of X-rays during radiography of the subject. The subject is radiographed in order to produce data. The data is used to calculate the projective length pro_pt of the subject and the projective length pro_ex of the non-subject entities having affected the data. The information associated with the projective length pro_pt of the subject and the projective length pro_ex of the non-subject entities is read out and used to correct the data in order to compensate scattering.

In the scattering compensating method according to the second aspect, a subject is radiographed in order to produce data. The data is used to calculate the projective length pro_pt of the subject and the projective length pro_ex of non-subject entities having affected the data. Information stored in association with the projective length pro_pt of the subject and the projective length pro_ex of the non-subject entities is read out. Consequently, an amount of scattering can be inferred from the information. Eventually, the produced data can be corrected in order to compensate scattering.

According to the third aspect of the present invention, there is provided a scattering compensating method identical to the scattering compensating method in accordance with the first or second aspect except that the information refers to a scattering function f(pro_pt+pro_ex) for use in calculating the amount of scattering S(do,d) on the basis of a sum of projective lengths pro_pt+pro_ex, that is, the sum of the projective length pro_ex of the non-subject entities and the projective length pro_pt of the object of radiography.

In the scattering compensating method according to the third aspect, the scattering function f(pro_pt+pro_ex) stored in association with the sum pro_pr+pro_ex of the projective length pro_pt of the subject and the projective length pro_ex of the non-subject entities is read out. Consequently, the amount of scattering S(do,d) can be calculated using the scattering function f(pro_pt+pro_ex). Eventually, the produced data can be corrected in order to compensate scattering.

According to the fourth aspect of the present invention, there is provided a scattering compensating method identical to the scattering compensating method according to the third aspect except that the scattering function f(pro_pt+pro_ex) is an an n-th-order function (where n≧1) of the sum of projective lengths pro_pt+pro_ex. The information refers to all or part of coefficients a0, . . . , an, included in the n-th-order function.

In the foregong method, part of the coefficients a0, . . . , an signifies that a coefficient of a value 0 need not be stored. For example, but for a constant term, the coefficient a0 need not be stored.

In the scattering compensating method according to the fourth aspect, once the coefficients a0, . . . , an, stored in association with the sum pro_pt+pro_ex of the projective length pro_pt of the subject and the projective length pro_ex of the non-subject entities are read out, the amount of scattering S(do,d) can be calculated using an n-th-order function defined with the read coefficients. Eventually, the produced data can be corrected in order to compensate scattering.

According to the fifth aspect of the present invention, there is provided a scattering compensating method identical to the scattering compensating method in accordance with any of the first to fourth aspects except that the information is used to calculate an amount of scattering relative to each detector distinguished with a detector array number and a channel number, and the amount of scattering is subtracted from the data produced by each detector. Thus, the data is corrected in order to compensate scattering.

Since the amount of scattering is subtracted from the produced data, the adverse effect of scattering can be suppressed.

According to the sixth aspect of the present invention, there is provided a scattering compensating method identical to the scattering compensating method in accordance with any of the first to fifth aspects except that the information is stored in association with two or more different values of at least one of an X-ray tube output Io, a detector thickness do, a beam thickness d, a detector array number r, and a channel number ch.

In the scattering compensating method according to the sixth aspect, for example, even when the X-ray tube output Io, the detector thickness do, or the beam thickness d is modified, scattering can be compensated accordingly.

According to the seventh aspect of the present invention, there is provided a scattering measuring method comprising: a step of acquiring the projective length pro_ex of non-subject entities that are entities other than a subject, the entities causing scattering of X-rays which cannot be ignored while existing in the passage of X-rays during radiography of the subject; a step of acquiring the projective length pro_pt of an object of radiography; a step of inserting the non-subject entities and the object of radiography into the passage of X-rays, measuring data I(do,do) by performing radiography with a beam thickness set to the same value as a detector thickness do, measuring data I(do,d) by radiographing the object of radiography with the beam thickness set to a value d larger than the detector thickness do, and calculating an amount of scattering S(do,d) on the basis of the difference between the data I(do,do) and the data I(do,d); and a step of storing information needed to calculate the amount of scattering S(do,d) using the projective length pro_ex of the non-subject entities and the projective length pro_pt of the object of radiography.

In the scattering measuring method according to the seventh aspect, the detector thickness do is held unchanged but the beam thickness d alone is modified. Therefore, an increment from the data I(do,do) to the data I(do,d) is thought to attribute to scattering. Consequently, the amount of scattering S(do,d) can be calculated based on the difference between the data I(do,do) and the data I(do,d). Incidentally, scattering represented by the data I(do,do) is ignored. Otherwise, since the data I(do,do) can be regarded as data produced by a single-channel detector, the conventional scattering compensating method may be used to correct the information on scattering contained in the data I(do,do).

Scattering of X-rays occurring during radiography of a subject is caused by non-subject entities such as a filter and covers existing in the passage of X-rays, and the subject. The projective length proj_ex of the non-subject entities (equal to a product of an X-ray absorption coefficient by an X-ray transmissive length) and the projective length pro_pt of the subject express the property of the non-subject entities and the project of the subject respectively, and are thought to correlate with the amount of scattering S(do,d). Therefore, the correlation among the projective length pro_ex of the non-subject entities, the projective length pro_pt of the object of radiography, and the amount of scattering S(do,d) is defined, and the information on the correlation is stored in association with the projective length pro_ex of the non-subject entities and the projective length pro_pt of the object of radiography.

As the information on the correlation, the amount of scattering S(do,d) may be directly stored. Otherwise, so-called indirectly, a function formula for use in calculating the amount of scattering S(do,d) using the projective length pro_ex of the non-subject entities and the projective length pro_pt of the object of radiography, or parameters (coefficients or the like) defining the function formula may be stored. Otherwise, the ratio of the amount of scattering S(do,d) to data or a value calculated by subtracting the ratio from 1, that is, the ratio of the value calculated by subtracting the amount of scattering S(do,d) from the data may be stored.

Moreover, the information on the correlation may be stored in so-called indirect association with a parameter calculated from the projective length pro_ex of the non-subject entities and the projective length pro_pt of the object of radiography instead of being stored in direct association with the projective length pro_ex of the non-subject entities and the projective length pro_pt of the object of radiography. The parameter may be, for example, a sum of projective lengths pro_pt+pro_ex, that is, the sum of the projective length pro_ex of the non-subject entities and the projective length pro_pt of the object of radiography (information on each detector). Otherwise, the parameter may be a value calculated by adding up the sums of projective lengths pro_pt+pro_ex calculated relative to detectors belonging to all detector arrays and being included in the channel in which a detector concerned is included (information on each channel), a value calculated by adding up the sums of projective lengths pro_pt+pro_ex calculated relative to detectors that belong to a plurality of detector arrays including the detector array to which the detector concerned belongs and that are included in the channel in which the detector concerned is included (information on each detector), a value calculated by adding up the sums of projective lengths pro_pt+pro_ex calculated relative to detectors that are included in all channels and that belong to the detector array to which the detector concerned belongs (information on each detector array), a value calculated by adding up the sums of projective lengths pro_pt+pro_ex calculated relative to detectors that are included in a plurality of channels including the channel in which the detector concerned is included and that belong to the detector array to which the detector concerned belongs (information relative to each detector), a value calculated by adding up the sums of projective lengths pro_pt+pro_ex calculated relative to detectors that are included in a plurality of channels including the channel in which the detector concerned is included and that belong to a plurality of detector arrays including the detector array to which the detector concerned belongs (information on each detector), or a value calculated by adding up the sums of projective lengths pro_pt+pro_ex calculated relative to all detectors (information shared by all the detectors).

According to the eighth aspect of the present invention, there is provided a scattering measuring method identical to the scattering measuring method in accordance with the seventh aspect except that the step of acquiring the projective length pro_ex of the non-subject entities is a step of measuring data I_exout by performing radiography with the non-subject entities not inserted in the passage of X-rays, measuring data I_exin by performing radiography with the non-subject entities inserted in the passage of X-rays, and calculating the projective length pro_ex of the non-subject entities using the data I_exout and the data I_exin.

In the scattering measuring method according to the eighth aspect, the data I_exout is measured with the non-subject entities not inserted in the passage of X-rays, and the data I_exin is measured with the non-subject entities inserted in the passage of X-rays. Therefore, the difference between the data I_exout and the data I_exin is thought to attribute to the projective length pro_ex of the non-subject entities. Consequently, the projective length pro_ex of the non-subject entities can be calculated using the data I_exout and the data I_exin.

According to the ninth aspect of the present invention, there is provided a scattering measuring method identical to the scattering measuring method in accordance with the seventh aspect except that the step of acquiring the projective length pro_ex of the non-subject entities is a step of calculating the projective length pro_ex of the non-subject entities on the basis of the materials and shapes of the non-subject entities.

In the scattering measuring method according to the ninth aspect, an X-ray absorption coefficient is learned based on the materials of the non-subject entities, and an X-ray transmissive length is inferred from the shapes thereof. The projective length pro_ex of the non-subject entities can be calculated by multiplying the X-ray absorption coefficient by the X-ray transmissive length.

According to the tenth aspect of the present invention, there is provided a scattering measuring method identical to the scattering measuring method in accordance with any of the seventh to ninth aspects except that the step of acquiring the projective length pro_pt of the object of radiography is a step of measuring data I_ptout by performing radiography with the object of radiography not inserted in the passage of X-rays, measuring data I_ptin by radiographing the object of radiography with the object of radiography inserted in the passage of X-rays, and calculating the projective length pro_pt of the object of radiography using the data I_ptout and the data I_ptin.

In the scattering measuring method according to the tenth aspect, the data I_ptout is measured with the object of radiography not inserted in the passage of X-rays, and the data I_ptin is measured with the object of radiography inserted therein. Consequently, the difference between the data I_ptout and the data I_ptin is thought to attribute to the projective length pro_pt of the object of radiography. Consequently, the projective length pro_pt of the object of radiography can be calculated using the data I_ptout and the data I_ptin.

According to the eleventh aspect of the present invention, there is provided a scattering measuring method identical to the scattering measuring method in accordance with any of the seventh to tenth aspects except that a scattering function f(pro_pt+pro_ex) for use in calculating the amount of scattering S(do,d) on the basis of the sum of projective lengths pro_pt+pro_ex, that is, the sum of the projective length pro_ex of the non-subject entities and the projective length pro_pt of the object of radiography is defined and stored as the information.

In the scattering measuring method according to the eleventh aspect, the scattering function f(pro_pt+pro_ex) for use in calculating the amount of scattering S(do,d) on the basis of the sum pro_pt+pro_ex of the projective length pro_pt of the subject and the projective length pro_ex of the non-subject entities is defined and stored. Once the scattering function f(pro_pt+pro_ex) is read out, the amount of scattering S(do,d) can be calculated. Eventually, produced data can be corrected in order to compensate scattering.

According to the twelfth aspect of the present invention, there is provided a scattering measuring method identical to the scattering measuring method in accordance with the eleventh aspect except that the scattering function f(pro_pt+pro_ex) is an n-th-order function (where n≧1) of the sum of projective lengths pro_pt+pro_ex, and that all or part of coefficients a0, . . . , an, defining the n-th-order function are stored as the information.

In the foregoing method, part of the coefficients a0, . . . ,an signifies that a coefficient of a value of 0 need not be stored. For example, but for a constant term, the coefficient a0 need not be stored.

In the scattering measuring method according to the twelfth aspect, the coefficients a0, . . . , an, defining the n-th-order function f(pro_pt+pro_ex) for use in calculating the amount of scattering S(do,d) on the basis of the sum pro_pt+pro_ex of the projective length pro_pt of the subject and the projective length pro_ex of the non-subject entities are calculated and stored. Once the coefficients a0, . . . ,an are read out, the amount of scattering S(do,d) can be calculated using the n-th-order function f(pro_pt+pro_ex). Eventually, produced data can be corrected in order to compensate scattering.

According to the thirteenth aspect of the present invention, there is provided a scattering measuring method identical to the scattering measuring method in accordance with any of the seventh to twelfth aspects except that measurement is performed with at least one of an X-ray tube output Io, a detector thickness do, a beam thickness d, a detector array number r, and a channel number ch being set to two or more different values, and the information is stored in association with each of the values.

In the scattering measuring method according to the thirteenth aspect, for example, even when the X-ray tube output Io, the detector thickness do, or the beam thickness d is modified, scattering can be compensated accordingly.

According to the fourteenth aspect of the present invention, there is provided an X-ray CT system comprising: an X-ray tube; a multi-channel X-ray detector; a scanning means for producing data while relatively rotating at least one of the X-ray tube and multi-channel X-ray detector about a subject; a projective length-of-non-subject entities acquiring means for acquiring the projective length pro_ex of non-subject entities that are entities other than a subject, the entities causing scattering of X-rays which cannot be ignored while existing in the passage of X-rays during radiography of the subject; a projective length-of-object-of-radiography acquiring means for acquiring the projective length pro_pt of the object of radiography; an amount-of-scattering acquiring means for inserting the non-subject entities and the object of radiography in the passage of X-rays, measuring data I(do,do) by performing radiography with a beam thickness set to the same value as a detector thickness do, measuring data I(do,d) by radiographing the object of radiography with the beam thickness set to a value d larger than the detector thickness do, and calculating an amount of scattering S(do,d) on the basis of the difference between the data I(do,do) and the data I(do,d); an information storing means for storing information needed to calculate the amount of scattering S(do,d) using the projective length pro_ex of the non-subject entities and the projective length pro_pt of the object of radiography; and a scattering compensating means for irradiating an X-ray beam having the beam thickness d so as to produce data using a detector having the detector thickness do, using the data to calculate the projective pro_pt of the subject and the projective length pro_ex of the non-subject entities having affected the data, reading information associated with the projective lengths, and using the information to correct data in order to compensate scattering.

In the X-ray CT system according to the fourteenth aspect, the detector thickness do is held unchanged but the beam thickness d alone is modified. Consequently, the increment from the data I(do,do) to the data I(do,d) is thought to attribute to scattering. Therefore, the amount of scattering S(do,d) can be calculated based on the difference between the data I(do,do) and the data I(do,d). At this time, scattering represented by the data I(do,do) is ignored. Otherwise, since the data I(do,do) can be regarded as data produced by a single-channel X-ray detector, the conventional scattering compensating method may be adopted in order to further correct the information on scattering contained in the data I(do,do).

Scattering of X-rays occurring during radiography of a subject is caused by non-subject entities such as a filter and covers existent in the passage of X-rays, and a subject. The projective length proj_ex of the non-subject entities and the projective length pro_pt of the subject express the property of the non-subject entities and the property of the subject respectively, and are thought to correlate with the amount of scattering S(do,d). Consequently, the correlation among the projective length pro_ex of the non-subject entities, the projective length pro_pt of the object of radiography, and the amount of scattering S(do,d) is defined, and the information on the correlation is stored in association with the projective length pro_ex of the non-subject entities and the projective length pro_pt of the object of radiography.

As the information, the amount of scattering S(do,d) itself may be stored directly. Otherwise, so-called indirectly, a function formula for use in calculating the amount of scattering S(do,d) using the projective length pro_ex of the non-subject entities and the projective length pro_pt of the object of radiography or a parameter (coefficient or the like) defining the function formula may be stored. Otherwise, the ratio of the amount of scattering S(do,d) to data or a value calculated by subtracting the ratio from 1, that is, the ratio of a value calculated by subtracting the amount of scattering S(do,d) from the data may be stored.

Moreover, the information on the correlation may be stored in so-called indirect association with a parameter determined with the projective length pro_ex of the non-subject entities and the projective length pro_pt of the object of radiography instead of being stored in direct association with the projective length pro_ex of the non-subject entities and the projective length pro_pt of the object of radiography. As the parameter, a sum of projective lengths pro_pt+pro_ex, that is, the sum of the projective length pro_ex of the non-subject entities and the projective length pro_pt of the object of radiography may be adopted (information on each detector). Otherwise, the parameter may be a value calculated by adding up sums of projective lengths pro_pt+pro_ex calculated relative to detectors that are included in the channel in which a detector concerned is included and the belong to all detector arrays (information relative to each channel), a value calculated by adding up sums of projective lengths pro_pt+pro_ex calculated relative to detectors that belong to a plurality of detector arrays including the detector array to which the detector concerned belongs and that are included in the channel in which the detector concerned is included (information relative to each detector), a value calculated by adding up sums of projective lengths pro_pt+pro_ex calculated relative to detectors that are included in all channels and that belong to the detector array to which the detector concerned belongs (information on each detector array), a value calculated by adding up sums of projective lengths pro_pt+pro_ex calculated relative to detectors that are included in a plurality of channels including the channel in which the detector concerned is included and that belong to the detector array to which the detector concerned belongs (information on each detector), a value calculated by adding up sums of projective lengths pro_pt+pro_ex calculated relative to detectors that are included in a plurality of channels including the channel in which the detector concerned is included and that belong to a plurality of detector arrays including the detector array to which the detector concerned belongs (information on each detector), or a value calculated by adding up sums of projective lengths pro_pt+pro_ex calculated relative to all detectors (information shared by all the detectors).

A subject is radiographed in order to produce data. The data is used to calculate the projective length pro_pt of the subject and the projective length pro_ex of non-subject entities having affected the data (the projective length pro_ex is determined with the geometric relationship between a detector having produced the data and the non-subject entities). Once information stored in association with the projective length pro_pt of the subject and the projective length pro_ex of the non-subject entities is read out, an amount of scattering can be inferred from the information. Eventually, the produced data can be corrected in order to compensate scattering.

According to the fifteenth aspect of the present invention, there is provided an X-ray CT system comprising: an X-ray tube; a multi-channel X-ray detector; a scanning means for producing data while relatively rotating at least one of the X-ray tube and the multi-channel X-ray detector about a subject; an information storing means for storing information needed to calculate an amount of scattering S(do,d) using the projective length pro_ex of non-subject entities that are entities other than the subject and the projective length pro_pt of the object of radiography, the entities causing scattering of X-rays which cannot be ignores while existing in the passage of X-rays during radiography of the subject; and a scattering compensating means for radiographing the subject so as to produce data, using the data to calculate the projective length pro_pt of the subject and the projective length pro_ex of the non-subject entities having affected the data, reading the information associated with both the projective lengths, and using the information to correct the data so as to compensate scattering.

In the X-ray CT system according to the fifteenth aspect, a subject is radiographed in order to produce data. The data is used to calculate the projective length pro_pt of the subject and the projective length pro_ex of the non-subject entities having affected the data. Once the information stored in association with the projective length pro_pt of the subject and the projective length pro_ex of the non-subject entities is read out, an amount of scattering can be inferred from the information. Eventually, produced data can be corrected in order to compensate scattering.

According to the sixteenth aspect of the present invention, there is provided an X-ray CT system identical to the X-ray CT system in accordance with the fourteenth or fifteenth aspect except that the information refers to a scattering function f(pro_pt+pro_ex) for use in calculating the amount of scattering S(do,d) on the basis of a sum of projective lengths pro_pt+pro_ex, that is, the sum of the projective length pro_ex of the non-subject entities and the projective length pro_pt of the subject.

In the X-ray CT system according to the sixteenth aspect, once the scattering function f(pro_pt+pro_ex) stored in association with the sum pro_pt+pro_ex of the projective length pro_pt of the subject and the projective length pro_ex of the non-subject entities is read out, the amount of scattering S(do,d) can be calculated using the scattering function f(pro_pt+pro_ex). Eventually, the produced data can be corrected in order to compensate scattering.

According to the seventeenth aspect of the present invention, there is provided an X-ray CT system identical to the X-ray CT system in accordance with the sixteenth aspect except that the scattering function f(pro_pt+pro_ex) is an n-th-order function (where n≧1) of the sum of projective lengths pro_pt+pro_ex, and the information refers to all or part of coefficients a0, . . . , an defining the n-th-order function.

In the foregoing system, part of coefficients a0, ..., an signifies that a coefficient having a value of 0 need not be stored. For example, but for a constant term, the coefficient a0 need not be stored.

In the X-ray CT system according to the seventeenth aspect, the coefficients a0, ..., an defining the n-th-order function f(pro_pt+pro_ex) for use in calculating the amount of scattering S(do,d) on the basis of the sum pro_pt+pro_ex of the projective length pro_pt of the subject and the projective length pro_ex of the non-subject entities are calculated and stored. Once the coefficients a0, ..., an are read out, the amount of scattering S(do,d) can be calculated using the n-th-order function f(pro_pt+pro_ex). Eventually, the produced data can be corrected in order to compensate scattering.

According to the eighteenth aspect of the present invention, there is provided an X-ray CT system identical to the X-ray CT system in accordance with any of the fourteenth to, seventeenth aspects except that the scattering compensating means uses the information to calculate an amount of scattering relative to each detector distinguished with a detector array number and a channel number, and subtracts the amount of scattering from the data produced by each detector. Thus, the data is corrected in order to compensate scattering.

By subtracting the amount of scattering from the data, the adverse effect of scattering can be suppressed.

According to the nineteenth aspect of the present invention, there is provided an X-ray CT system identical to the X-ray CT system in accordance with any of the fourteenth to eighteenth aspects except that the information storing means stores the information in association with two or more different values of at least one of an X-ray tube output Io, a detector thickness do, a beam thickness d, a detector array number r, and a channel number ch.

In the X-ray CT system according to the nineteenth aspect, for example, even when the X-ray tube output Io, detector thickness do, or beam thickness d is modified, scattering can be compensated.

According to a scattering compensating method and an X-ray CT system in which the present invention is implemented, scattering occurring during multi-slice radiography can be compensated.

Moreover, according to a scattering measuring method and an X-ray CT system in which the present invention is implemented, scattering occurring during multi-slice radiography can be measured.

Further objects and advantages of the present invention will be apparent from the following description of the preferred embodiments of the invention as illustrated in the accompanying drawings.

BRIEF DESCRIPTION OF THE DRAWINGS

FIG. 2 is a flowchart describing scattering measurement employed in the first embodiment.

FIG. 3 is an explanatory diagram showing the circumstances under which scattering measurement is performed.

FIG. 4 is a conceptual diagram showing a form of storing the projective length of non-subject entities.

FIG. 5 is a conceptual diagram showing a form of storing scattering coefficients.

FIG. 6 is an explanatory diagram showing the circumstances under which radiography of a subject is performed.

DETAILED DESCRIPTION OF THE INVENTION

The present invention will be further described below by presenting illustrated embodiments. Noted is that the present invention is not limited to the embodiments.

First Embodiment

Figure 1:
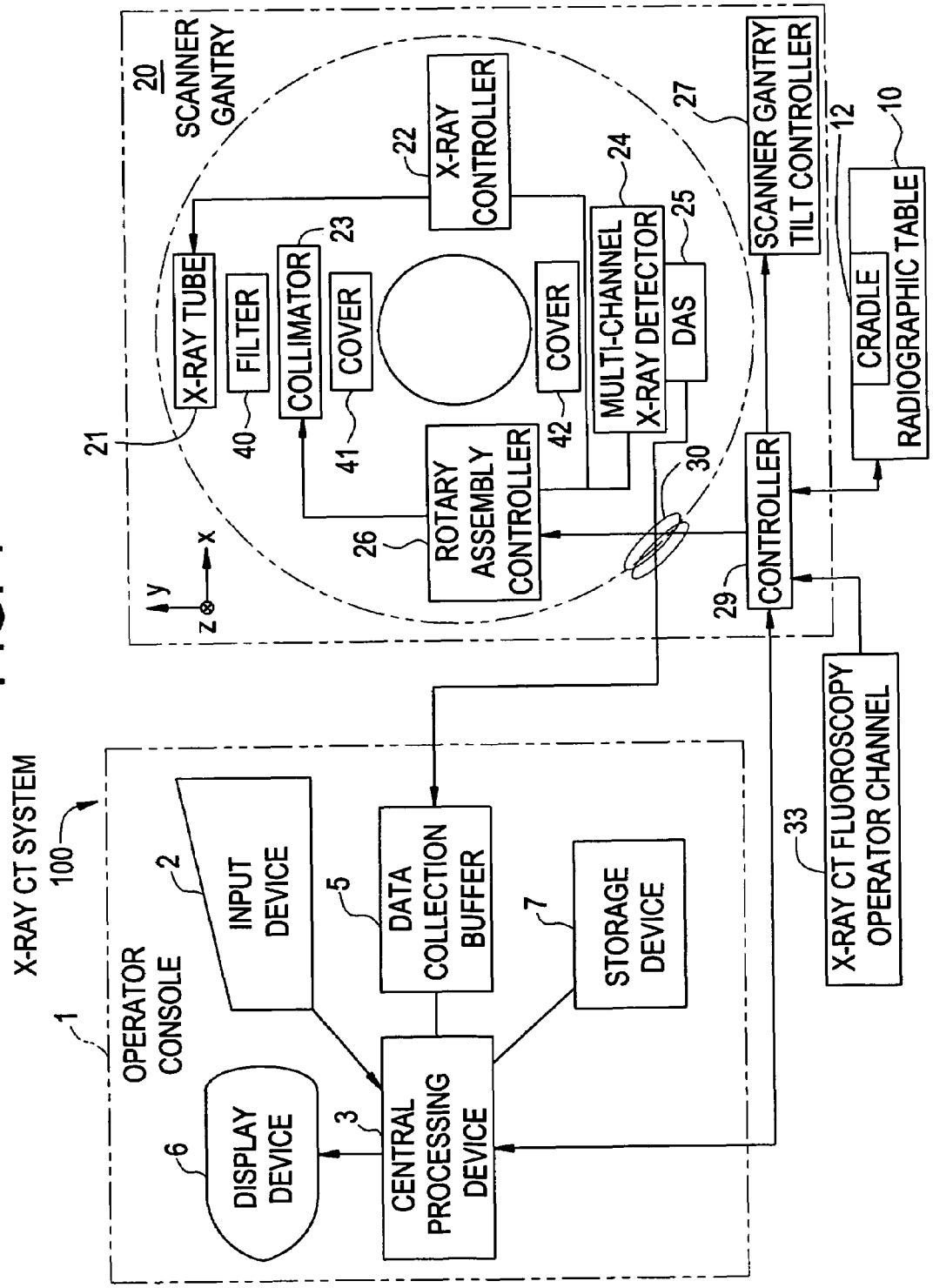
FIG. 1 is a block diagram showing an X-ray CT system in accordance with the first embodiment.

FIG. 1 is a block diagram showing the configuration of an X-ray CT system 100 in accordance with the first embodiment.

The X-ray CT system 100 comprises an operator console 1, a radiographic table 10, and a scanner gantry 20.

The operator console 1 comprises an input device 2 that receives an operator's entry, a central processing device 3 that performs scattering measurement, scan processing, scattering compensation, preprocessing, image reconstruction, and post-processing, a data collection buffer 5 that collects data acquired by the scanner gantry 20, a display device 6 on which tomographic images reconstructed based on projection data produced by preprocessing the collected data are displayed, and a storage device 7 in which programs, data, and tomographic images are stored.

The radiographic table 10 includes a cradle 12 on which a subject lies down and which carries the subject into or out of the bore of the scanner gantry 20. The cradle 12 is raised or lowered and rectilinearly moved by a motor incorporated in the radiographic table 10.

The scanner gantry 20 comprises an X-ray tube 21, an X-ray controller 22, a collimator 23, a multi-channel X-ray detector 24, a data acquisition system (DAS) 25, a rotary assembly controller 26 that controls the X-ray tube 21 and others which rotate about a center axis of rotation, a controller 29 that transfers control signals and others to or from the operator console 1 and radiographic table 10, and a slip ring 30 that transfers power, control signals, and produced data. Moreover, a scanner gantry tilt controller 27 permits the scanner gantry 20 to tilt ±30° forward or backward.

A filter 40 and covers 41 and 42 are located in the passage of X-rays. The filter and covers are non-subject entities that are entities other than a subject causing scattering of X-rays, which cannot be ignored, while existing in the passage of X-rays during radiography of the subject.

FIG. 2 is a flowchart describing scattering measurement in accordance with the first embodiment.

At step P1, as shown in FIG. 3(a), air is radiographed with a beam thickness do set to the same value as a detector thickness do of a detector det(r,ch,do) with the filter 40 and covers 41 and 41, that is, the non-subject entities dismounted. Consequently, data I(Io,θ,r,ch,do,do,exout) is produced.

Parameters r, ch, and do used to distinguish a detector det(r,ch,do) denote a detector array number, a channel number, and a detector thickness respectively.

Moreover, parameters Io, θ, r, ch, do, do, and exout used to distinguish data I(Io,θ,r,ch,do,do,exout) denote an X-ray tube output, a view angle, a detector array number, a channel number, a detector thickness, a beam thickness, and absence of non-subject entities.

At step P2, as shown in FIG. 3(b), the filter 40 and covers 41 and 42, that is, the non-subject entities are mounted, and air is radiographed with the beam thickness set to the same value do as the detector thickness do of the detector det(r,ch,do). Consequently, data I(Io,θ,r,ch,do,do,exin) is produced.

Incidentally, a parameter exin included in the parameters used to distinguish data I(Io,θ,r,ch,do,do,exin) signifies presence of non-subject entities.

At step P3, as shown in FIG. 3(c), a phantom α is radiographed with the beam thickness set to the same value do as the detector thickness do of the detector det(r,ch,do) in order to produce data I(Io,θ,r,ch,do,do,pt). This procedure is repeated using phantoms α having different sizes.

Incidentally, a parameter pt included in the parameters used to distinguish data I(Io,θ,r,ch,do,do,pt) signifies presence of a phantom and non-subject entities.

At step P4, as shown in FIG. 3(d), the phantom α is radiographed with the beam thickness set to a value d larger than the detector thickness do of the detector det(r,ch,do) in order to produce data I(Io,θ,r,ch,do,d,pt). This procedure is repeated using the phantoms a of different sizes.

At step P5, the projective length pro_ex(θ,r,ch) of non-subject entities is calculated using the data I(Io,θ,r,ch,do,do,exout) and the data I(Io,θ,r,ch,do,do,exin), and then stored as shown in FIG. 4.

$$pro\_ex(\theta,r,ch) = -\log\{I(Io,\theta,r,ch,do,do,exin)/I(Io,\theta,r,ch,do,do,exout)\}$$

At step P6, the projective length pro_pt(θ,r,ch) of the phantom α is calculated using the data I(Io,θ,r,ch,do,do,exin) and the data I(Io,θ,r,ch,do,do,pt). This procedure is repeated using data items produced by radiographing the phantoms α of different sizes, whereby different projective lengths pro_pt(θ,r,ch) are worked out.

$$pro\_pt(\theta,r,ch) = -\log\{I(Io,\theta,r,ch,do,do,pt)/I(Io,\theta,r,ch,do,do,exin)\}$$

At step P7, the difference between the data I(Io,θ,r,ch,do,do,pt) and the data I(Io,θ,r,ch,do,d,pt) is calculated as an amount of scattering S(Io,θ,r,ch,do,d,pt). This procedure is repeated using data items produced by radiographing the phantoms α of different sizes, whereby the amounts of scattering S are worked out in association with different projective lengths pro_pt(θ,r,ch).

$$S(Io,\theta,r,ch,do,d,pt) = I(Io,\theta,r,ch,do,d,pt) - I(Io,\theta,r,ch,do,do,pt)$$

At step P8, the amount of scattering S is fitted to or approximated to an n-th-order function of a sum of projective lengths W=pro_pt(θ,r,ch)+pro_ex(θ,r,ch), that is, the sum of the projective length pro_ex(θ,r,ch) of the non-subject entities and the projective length pro_pt(θ,r,ch) of the phantom α, whereby coefficients a0, . . . , an, defining the n-th-order function are calculated and stored as shown in FIG. 5.

$$S = a0 + a1 \cdot W + a2 \cdot W^2 + a3 \cdot W^3 + \ldots + an \cdot W^n$$

FIG. 6 is a conceptual diagram showing the radiographic state of a subject.

First, as shown in FIG. 6(a), radiography is performed without a subject in order to produce calibration data I(Io,θ,r,ch,do,d,air).

Thereafter, as shown in FIG. 6(b), a subject β is inserted and radiographed in order to produce tomographic image reconstruction data I(Io,θ,r,ch,do,d,pt).

Figure 7:
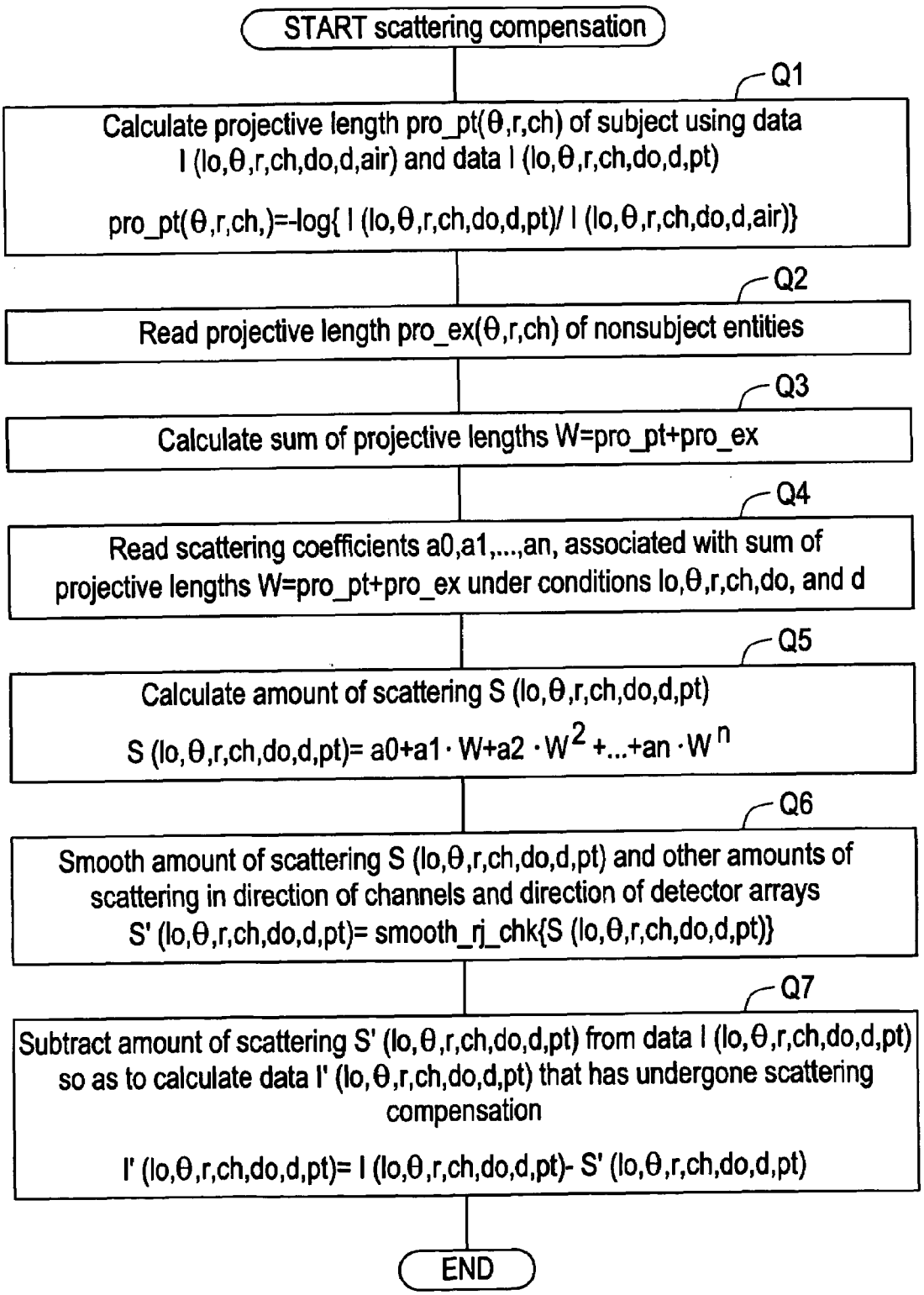
FIG. 7 is a flowchart describing scattering compensation employed in the first embodiment.

FIG. 7 is a flowchart describing scattering compensation employed in the first embodiment.

At step Q1, the projective length pro_pt(θ,r,ch) of the subject β is calculated using the calibration data I(Io,θ,r,ch,do,d,air) and the tomographic image reconstruction data I(Io,θ,r,ch,do,d,pt).

$$pro\_pt(\theta,r,ch) = -\log\{I(Io,\theta,r,ch,do,d,pt)/I(Io,\theta,r,ch,do,d,air)\}$$

At step Q2, the projective length pro_ex(θ,r,ch) of the non-subject entities is read out.

At step Q3, the sum of projective lengths W=pro_pt(θ,r,ch)+pro_pt(θ,r,ch) is calculated.

At step Q4, scattering coefficients a0, a1, . . . , an, that are associated with the sum of projective lengths W=pro_pt+pro_pt under the conditions Io, θ, r, ch, do, and d are read out.

At step Q5, the read coefficients a0, a1, . . . , an, are used to calculate the amount of scattering S(Io,θ,r,ch,do,d,pt).

$$S = a0 + a1 \cdot W + a2 \cdot W^2 + a3 \cdot W^3 + \ldots + an \cdot W^n$$

At step Q6, the calculated amount of scattering S(Io,θ,r,ch,do,d,pt) and other amounts of scattering are smoothed in the direction of detector arrays and the direction of channels, whereby a smoothed amount of scattering S'(Io,θ,r,ch,do,d,pt) is worked out.

$$S'(Io,\theta,r,ch,do,d,pt) = \text{smooth\_rj\_chk}\{S(Io,\theta,r,ch,do,d,pt)\}$$

Herein, smooth_rj_chk{S(Io,θ,r,ch,do,d,pt)} is a function (for example, a function for providing a mean value) for smoothing amounts of scattering S(Io,θ,r−j,ch,do,d,pt) to S(Io,θ,r+j,ch,do,d,pt) calculated relative to detectors det(r−j,ch,do) to del(r+j,ch,do) that are included in the same channel and that are located in the range of ±j in the direction of detector arrays with a detector det(r,ch,do), relative to which the amount of scattering S(Io,θ,r,ch,do,d,pt) is calculated, as a center. Moreover, according to the function smooth_rj_chk{S(Io,θ,r,ch,do,d,pt)}, amounts of scattering S(Io,θ,r,ch−k,do,d,pt) to S(Io,θ,r,ch+k,do,d,pt) calculated relative to detectors det(r,ch−k,do) to det(r,ch+k,do) that belong to the same detector array and that are located in the range of ±k in the direction of channels with the detector det(r,ch,do), relative to which the amount of scattering S(Io,θr,ch,do,d,pt) is calculated, as a center are smoothed.

At step Q7, the amount of scattering S'(Io,θ,r,ch,do,d,pt) is subtracted from the tomographic image reconstruction data I(Io,θ,r,ch,do,d,pt) in order to calculate tomographic image reconstruction data I'(Io,θ,r,ch,do,d,pt) that has undergone scattering compensation. Scattering compensation is then terminated.

$$I'(Io,\theta,r,ch,do,d,pt) = I(Io,\theta,r,ch,do,d,pt) - S'(Io,\theta,r,ch,do,d,pt)$$

According to the first embodiment, a tomographic image reconstructed based on the tomographic image reconstruction data I'(Io,θ,r,ch,do,d,pt), which has undergone scattering compensation, enjoys improved image quality to gain an advantage over a tomographic image reconstructed based on tomographic image reconstruction data I(Io,θ,r,ch,do,d,pt) that has not undergone scattering compensation. When n is set to 4 and a0 is set to 0, the result of scattering compensation is satisfactory (in this case, a0 need not be stored).

According to the first embodiment, scattering occurring during multi-slice radiography is measured and compensated in a preferred manner. This results in a multi-slice image having artifacts, which are attributable to scattering occurring during multi-slice radiography, suppressed.

Second Embodiment

According to the second embodiment, the projective length pro_ex of non-subject entities is calculated but not measured.

Figure 8:
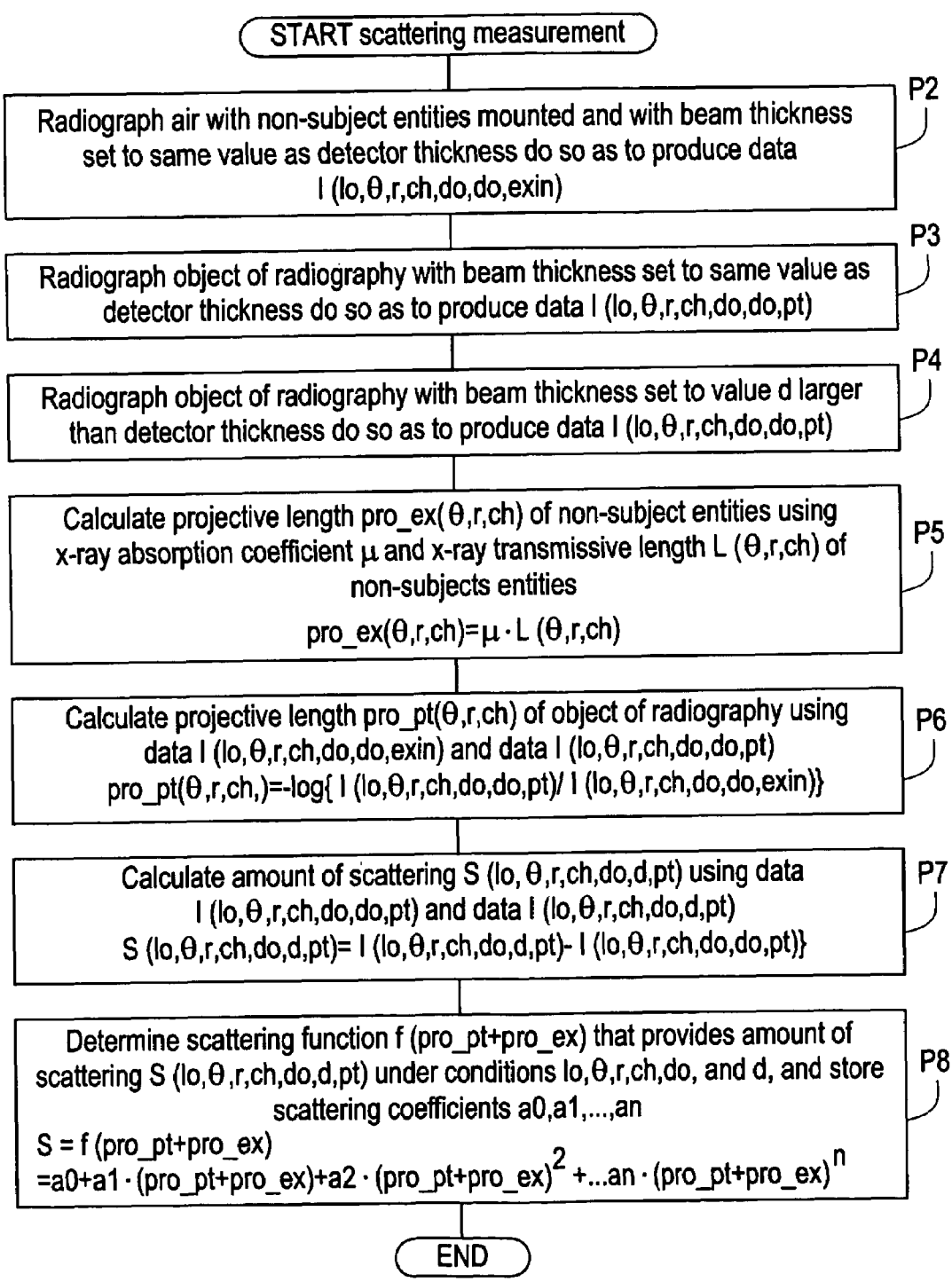
FIG. 8 is a flowchart describing scattering measurement employed in the second embodiment.

FIG. 8 is a flowchart describing scattering measurement employed in the second embodiment.

The scattering measurement employed in the second embodiment is different from the one (FIG. 2) employed in the first embodiment in points that step P1 is excluded and step P5' is substituted for step P5. Step P5' alone will be described below.

At step P5', the projective length pro_ex(θ,r,ch) of the non-subject entities is calculated based on an X-ray absorption coefficient μ and an X-ray transmissive length L(θ,r,ch) exhibited by the non-subject entities, and stored as shown in FIG. 4.

$$pro\_ex(\theta,r,ch)=\mu \cdot L(\theta,r,ch)$$

According to the second embodiment, it is unnecessary to acquire data with the non-subject entities dismounted.

Third Embodiment

According to the third embodiment, the coefficients a0, ..., an, defining the n-th-order function of the sum of projective lengths W to which the amount of scattering S is approximated are used in common among all views or all detectors.

Specifically, according to the first and second embodiments, the coefficients a0, ..., an defining the n-th-order function are calculated relative to each set of conditions Io, θ, r, ch, do, and d at step P8 (FIG. 2 of FIG. 8). According to the third embodiment, the coefficients a0, ..., an defining the n-th-order function are calculated relative to each set of conditions Io, do, and d and then stored.

According to the third embodiment, it is unnecessary to store the coefficients a0, ..., an in association with each view angle θ and each detector det(r,ch,do). This results in a simple procedure.

Fourth Embodiment

According to the first to third embodiments, the coefficients a0, ..., an defining the n-th-order function of the sum of projective lengths W, to which the amount of scattering S is approximated, are stored. Instead, an amount of scattering S(Io,θ,r,ch,do,d,pt) itself may be stored. Otherwise, the ratio of the amount of scattering S(Io,θ,r,ch,do,d,pt) to data I(Io,θ,r,ch,do,d,pt) (namely, the ratio of an amount of scattering to data) may be stored. Otherwise, a value calculated by subtracting the ratio of the amount of scattering S(Io,θ,r,ch,do,d,pt) to data I(Io,θ,r,ch,do,d,pt) from 1 may be stored.

Fifth Embodiment

According to the first to fourth embodiments, coefficients a0, ..., an are stored in association with a sum of projective lengths pro_pt+pro_ex, that is, the sum of the projective length pro_ex of non-subject entities and the projective length pro_pt of an object of radiography. Alternatively, the coefficients may be stored in direct association with the projective length pro_ex of the non-subject entities and the projective length pro_pt of the object of radiography. Otherwise, the coefficients may be stored in association with a value calculated by adding up the sums of projective lengths pro_pt+pro_ex calculated relative to detectors that are included in the channel in which a detector concerned is included and that belong to all detector arrays (information on each channel), a value calculated by adding up the sums of projective lengths pro_pt+pro_ex calculated relative to detectors that are included in the channel in which the detector concerned is included and that belong to a plurality of detector arrays including the detector array to which the detector concerned belongs (information on each detector), a value calculated by adding up the sums of projective lengths pro_pt+pro_ex calculated relative to detectors that belong to the detector array to which the detector concerned belongs and that are included in all channels (information on each detector array), a value calculated by adding up the sums of projective lengths pro_pt+pro_ex calculated relative to detectors that belong to the detector array to which the detector concerned belongs and that are included in a plurality of channels including the channel in which the detector concerned is included (information on each detector), a value calculated by adding up the sums of projective lengths pro_pt+pro_ex calculated relative to detectors that belong to a plurality of detector arrays including the detector array to which the detector concerned belongs and that are included in a plurality of channels including the channel in which the detector concerned is included (information on each detector), or a value calculated by adding up the sums of projective lengths pro_pt+pro_ex calculated relative to all detectors (information shared by all the detectors).

Many widely different embodiments of the invention may be constructed without departing from the spirit and the scope of the present invention. It should be understood that the present invention is not limited to the specific embodiments described in the specification, except as defined in the appended claims.

The invention claimed is:

1. A scattering compensating method comprising the steps of:
    acquiring a projective length pro_ex of non-subject entities that are entities other than a subject, the non-subject entities causing scattering of X-rays which cannot be ignored while existing in the passage of X-rays during radiography of the subject;
    acquiring a projective length pro_pt of an object of radiography;
    measuring data I(do,do) by performing radiography with the non-subject entities and the object of radiography inserted in the passage of X-rays and with a beam thickness set to the same value as a detector thickness do;
    measuring data I(do,d) by radiographing the object of radiography with the beam thickness set to a value d larger than the detector thickness do;
    calculating an amount of scattering S(do,d) on the basis of the difference between the data I(do,do) and the data I(do,d);
    storing information needed to calculate the amount of scattering S(do,d) using the projective length pro_ex of the non-subject entities and the projective length pro_pt of the object of radiography;
    using data produced by radiographing the subject to calculate the projective length pro_pt of the subject and the projective length pro_ex of the non-subject entities having affected the data;
    reading the information associated with the projective length pro_pt of the subject and the projective length pro_ex of the non-subject entities; and
    using the information to correct the data so as to compensate for scattering.

2. The scattering compensation method according to claim 1, wherein the information refers to a scattering function f(pro_pt+pro_ex) for use in calculating the amount of scattering S(do,d) on the basis of a sum of projective lengths pro_pt+pro_ex that is the sum of the projective length pro_ex of the non-subject entities and the projective length pro_pt of the object of radiography.

3. The scattering compensation method according to claim 2, wherein the scattering function f(pro_pt+pro_ex) is an n-th-order function (where n≧1) of a sum of projective lengths pro_pt+pro_ex, and the information refers to all or part of the coefficients a0, . . . , an, defining the n-th-order function.

4. The scattering compensation method according to claim 1 further comprising using the information to calculate an amount of scattering relative to each detector, each detector distinguished with a detector array number and a channel number, the amount of scattering is subtracted from the data produced by each detector.

5. The scattering compensation method according to claim 1 wherein storing information needed to calculate the amount of scattering further comprises storing information including information associated with two or more different values of at least one of an X-ray output Io, a detector thickness do, a beam thickness d, a detector array number r, and a channel number ch.

6. A scattering compensating method comprising the steps of:
storing information needed to calculate an amount of scattering S(do,d) using both a projective length pro_ex of non-subject entities that are entities other than a subject and a projective length pro_pt of an object of radiography, the non-subject entities causing scattering of X-rays which cannot be ignored while existing in the passage of X-rays during radiography of the subject;
using data produced by radiographing the subject to calculate the projective length pro_pt of the subject and the projective length pro_ex of the non-subject entities having affected the data;
reading the information associated with the projective length pro_pt of the subject and the projective length pro_ex of the non-subject entities; and
using the information to correct the data so as to compensate for scattering.

7. The scattering compensation method according to claim 6, wherein the information refers to a scattering function f(pro_pt+pro_ex) for use in calculating the amount of scattering S(do,d) on the basis of a sum of projective lengths pro_pt+pro_ex that is the sum of the projective length pro_ex of the non-subject entities and the projective length pro_pt of the object of radiography.

8. The scattering compensation method according to claim 7, wherein the scattering function f(pro_pt+pro_ex) is an n-th-order function (where n≧1) of a sum of projective lengths pro_pt+pro_ex, and the information refers to all or part of the coefficients a0, . . . , an, defining the n-th-order function.

9. The scattering compensation method according to claim 6 further comprising using the information to calculate an amount of scattering relative to each detector, each detector distinguished with a detector array number and a channel number, the amount of scattering is subtracted from the data produced by each detector.

10. The scattering compensation method according to claim 6 wherein storing information needed to calculate the amount of scattering further comprises storing information including information associated with two or more different values of at least one of an X-ray output Io, a detector thickness do, a beam thickness d, a detector array number r, and a channel number ch.

11. A scattering measuring method comprising:
acquiring a projective length pro_ex of non-subject entities that are entities other than a subject, the non-subject entities causing scattering of X-rays which cannot be ignored while existing in the passage of X-rays during radiography of the subject;
acquiring a projective length pro_pt of an object of radiography;
inserting the non-subject entities and the object of radiography in the passage of X-rays, measuring data I(do,do) by performing radiography with a beam thickness set to the same value as a detector thickness do, measuring data I(do,d) by radiographing the object of radiography with the beam thickness set to a value d larger than the detector thickness do, and calculating an amount of scattering S(do,d) on the basis of the difference between the data I(do,do) and the data I(do,d); and
storing information needed to calculate the amount of scattering S(do,d) using the projective length pro_ex of the non-subject entities and the projective length pro_pt of the object of radiography.

12. The scattering measuring method according to claim 11, wherein the step of acquiring the projective length pro_ex of the non-subject entities is a step of measuring data I_exout by performing radiography with the non-subject entities not inserted in the passage of X-rays, measuring data I_exin by performing radiography with the non-subject entities inserted in the passage of X-rays, and calculating the projective length pro_ex of the non-subject entities using the data I_exout and the data I_exin.

13. The scattering measuring method according to claim 12, wherein the step of acquiring the projective length pro_pt of the object of radiography is a step of measuring data I_ptout by performing radiography with the object of radiography not inserted in the passage of X-rays, measuring data I_ptin by performing radiography with the object of radiography inserted in the passage of X-rays, and calculating the projective length pr_pt of the object of radiography using the data I_ptout and the data I_ptin.

14. The scattering measuring method according to claim 11, wherein the step of acquiring the projective length pro_ex of the non-subject entities is a step of calculating the projective length pro_ex of the non-subject entities on the basis of the materials and shapes of the non-subject entities.

15. The scattering measuring method according to claim 14, wherein the step of acquiring the projective length pro_pt of the object of radiography is a step of measuring data I_ptout by performing radiography with the object of radiography not inserted in the passage of X-rays, measuring data I_ptin by performing radiography with the object of radiography inserted in the passage of X-rays, and calculating the projective length pr_pt of the object of radiography using the data I_ptout and the data I_ptin.

16. The scattering measuring method according to claim 11, wherein the step of acquiring the projective length pro_pt of the object of radiography is a step of measuring data I_ptout by performing radiography with the object of radiography not inserted in the passage of X-rays, measuring data I_ptin by performing radiography with the object of radiography inserted in the passage of X-rays, and calculating the projective length pr_pt of the object of radiography using the data I_ptout and the data I_ptin.

17. The scattering measuring method according to claim 16 wherein storing information needed to calculate the amount of scattering further comprises storing information referring to a scattering function f(pro_pt+pro_ex) for use in calculating the amount of scattering S(do,d) on the basis of the sum of projective lengths pro_pt+pro_ex that is the sum of the projective length pro_ex of the non-subject entities and the projective length pro_pt of the object of radiography.

18. The scattering measuring method according to claim 11 wherein storing information needed to calculate the amount of scattering further comprises storing information referring to a scattering function f(pro_pt+pro_ex) for use in calculating the amount of scattering S(do,d) on the basis of the sum of projective lengths pro_pt+pro_ex that is the sum of the projective length pro_ex of the non-subject entities and the projective length pro_pt of the object of radiography.

19. The scattering measuring method according to claim 18 further comprising calculating the amount of scattering using the scattering function and the stored information, the scattering function f(pro_pt+pro_ex) is an n-th-order function (where $n \geq 1$) of a sum of projective lengths pro_pt+pro_ex, and the information refers to all or part of the coefficients a0, . . . , an, defining the n-th-order function.

20. The scattering measuring method according to claim 11 wherein storing information needed to calculate the amount of scattering further comprises storing information including information associated with two or more different values of at least one of an X-ray output Io, a detector thickness do, a beam thickness d, a detector array number r, and a channel number ch.

* * * * *